United States Patent [19]

Dopatka et al.

[11] Patent Number: 4,988,629
[45] Date of Patent: Jan. 29, 1991

[54] LACTOFERRIN-CONTAINING INCUBATION MEDIUM FOR SOLID-PHASE IMMUNOMETRIC METHODS AND ITS USE

[75] Inventors: Hans-Detlef Dopatka; Rudolf Schmidtberger, both of Marburg, Fed. Rep. of Germany

[73] Assignee: Behringwerke Aktiengesellschaft, Marburg/Lahn, Fed. Rep. of Germany

[21] Appl. No.: 118,982

[22] Filed: Nov. 10, 1987

[30] Foreign Application Priority Data

Nov. 13, 1986 [DE] Fed. Rep. of Germany ....... 3638767
Apr. 15, 1987 [EP] European Pat. Off. .......... 87105621

[51] Int. Cl.$^5$ .............................................. G01N 33/53
[52] U.S. Cl. .................................. 436/518; 435/7.5; 435/7.92; 435/7.94; 435/962; 436/18; 436/176; 436/531; 436/538; 436/825; 436/826
[58] Field of Search ............... 436/533, 534, 825, 518, 436/18, 176, 531, 538, 826; 435/7

[56] References Cited

U.S. PATENT DOCUMENTS

| | | | |
|---|---|---|---|
| 4,184,849 | 1/1980 | Cambiaso | 436/523 |
| 4,248,965 | 2/1981 | Mochida et al. | |
| 4,253,844 | 3/1981 | Limet | 436/512 |
| 4,397,960 | 8/1983 | Moussebois | 436/512 |
| 4,436,658 | 3/1984 | Peyrouset | 530/832 X |
| 4,629,783 | 12/1986 | Cosand | 530/324 |
| 4,668,771 | 5/1987 | Kawakami | 530/832 X |
| 4,784,941 | 11/1988 | Watanabe et al. | 435/5 |

FOREIGN PATENT DOCUMENTS 61-145200  2/1986  Japan.
2074727  11/1981  United Kingdom.

OTHER PUBLICATIONS

Chem. Abstracts 85: No. 9 (8/30/76), "A Solid Phase Radioimmunoassay for the Measurement of Lactoferrin in Human Plasma: Variations with Age, Sex and Disease".
Chem. Abstracts 103: No. 19 (11/11/85), "Enzyme Linked Immunosorbent Assay for Lactoferrin".
European Search Report.
Johnson et al., "Improved Technique Utilizing Nonfat Dry Milk for Analysis of Proteins and Nucleic Acids Transferred to Nitrocellulose", Gene Analysis Techniques, 1(1) 1984, 3–8.

Primary Examiner—Christine Nucker
Attorney, Agent, or Firm—Finnegan, Henderson, Farabow, Garrett, and Dunner

[57] ABSTRACT

Incubation media intended for solid-phase immunometric assays and containing lactoferrin are described. Compared with the media used hitherto, these incubation media have the advantage that they prevent, especially in the case where heated sample material is used in the assays, false results on determination of antigens or antibodies.

9 Claims, No Drawings

LACTOFERRIN-CONTAINING INCUBATION MEDIUM FOR SOLID-PHASE IMMUNOMETRIC METHODS AND ITS USE

The invention relates to a lactoferrin-containing incubation medium for solid-phase immunometric assays and to the use of this medium.

For solid-phase immunometric assays, for example ELISA, the composition of the required incubation media ("buffer solutions", "incubation milieus") must be such that non-specific binding of concomitant substances in the sample to the solid phase is prevented. Additives known for this purpose are proteins such as albumin, casein, mixtures of proteins such as animal sera, hydrolyzed gelatin or its derivatives, as well as surfactants.

Incubation media provided with such additives are unable to prevent measurements being false, which particularly occurs when samples have been heated. Heating is expedient to reduce the infectiosity of the samples, which may derive from, for example, HIV (human immunodeficiency virus).

Hence the object was to find an incubation medium with which there is no occurrence, when it is used, of false values caused by heating of the sample.

It has been found, surprisingly, that an incubation medium which contains lactoferrin achieves this object.

The invention relates to an incubation medium for solid-phase immunometric assays containing lactoferrin.

The invention also relates to the use of lactoferrin in an incubation medium which is used for a solid-phase immunometric assay.

An incubation medium within the meaning of the invention is the liquid phase, in which the immunochemical reaction takes place of a solid-phase immunometric assay.

Lactoferrin is added in a concentration of from 0.05 to 20 g/l. A concentration of 0.15–0.25, in particular 0.2, g/l is preferred.

The lactoferrin can be added to incubation media or buffer solutions known per se for solid-phase immunometric assays. One of these is, for example, the solution described in German Patent A-27 448 36 on page 24, which, apart from buffer substance, contains 5 g/l bovine serum albumin, 5 g/l polyoxyethylene (20) sorbitan monolaurate (( ®)Tween 20) in phosphate-buffered physiological saline solution (PBS). Another example which may be mentioned is the solution described in German Patent A-31 15 115 on page 10, a 0.2 mol/l $NaH_2PO_4/Na_2HPO_4$ buffer, pH 6.5, which contains 2 g/l bovine serum albumin and 200 ml/l normal goat serum. A preferred buffer solution is used in example 1.

A medium of this type can advantageously contain a protein known per se, preferably casein, and/or a hydrolysis product of gelatin, or hydrolyzed and chemically treated gelatin.

The lactoferrin to be used according to the invention can be obtained from the milk of a mammal by removing the cream from the milk, adjusting the milk, from which the cream has been removed, to a pH of 3.5–4.5, removing the protein precipitate which has formed, and removing and isolating the lactoferrin from the supernatant by chromatography on an ion exchanger.

Lactoferrin is isolated from milk, preferably from cow's milk. In a preferred process for obtaining a lactoferrin suitable for the purpose according to the invention, the fat is removed from the milk by, for example, centrifuging it. The upper of the two phases which form is removed and discarded. The lower phase is adjusted to pH 3.5–4.5 with an acid. This results in a precipitate which is sedimented, for example by centrifugation, and is discarded. The supernatant is adjusted to a conductivity of 6–7 mS/cm by dilution with water. Then a cation exchanger, for example CM-cellulose or SP-®Sephadex, which has been swollen and equilibrated with a buffer of pH 4–5.5 and a conductivity of, preferably, 6–7 mS/cm is introduced. The suspension is filtered, and the residue is washed several times with the same buffer, and is then suspended therein and packed into a column. It is eluted with a gradient of, preferably, 0–1 mol/l NaCl at pH 5. The fraction which is eluted in the range 500–650 mmol/l NaCl as a homogeneous peak measured at 280 nm contains the lactoferrin which is particularly suitable for the incubation medium. On SDS-PAGE electrophoresis, this lactoferrin appears as a band with a molecular weight of $80,000 \pm 3,000$.

On chromatography on an anion exchanger, for example on DEAE- or QAE- ®Sephadex, or on DEAE-cellulose, the supernatant from the precipitation at pH 3.5–4.5 which has been described above is adjusted to pH 6.5–7.5 and a conductivity of 6–8 mS/cm, and is applied to a column packed with the ion exchanger which has previously been equilibrated with a buffer of pH 6.5–7.5 and a conductivity of 6–8 mS/cm. The lactoferrin then passes through the column or is eluted as the first peak on elution with an NaCl gradient.

The lactoferrin must be present on incubation of the sample or of the analyte with the reactants which are bound to the solid phase. It can be added to the solution which contains the analyte or to the solution or the buffer with which the analyte is diluted. However, it can also be contacted in dissolved form with the reactant which is bound to the solid phase and/or dried onto the solid phase before this is contacted with the analyte.

Suitable reactants which are bound to solid phases are the components of a bioaffinity binding system which are able to bind an analyte of this type. In the case of an immunological binding system, these reactants are either antigens or antibodies. Solid-phase immunometric assays can be both competitive and two-side immunometric (sandwich) assays or even indirect assays. In the latter case the analyte is an antibody, and the solid-phase reactant is the corresponding antigen, and the amount of antibody which is bound to the solid phase is determined by a second, labeled antibody.

The assay system can be a single-step or multistep assay.

The lactoferrin prevents the binding of those constituents of the sample which do not belong to the particular bioaffinity binding system. It thus averts false results in the detection and determination of the analyte.

The examples which follow illustrate the invention and demonstrate the appropriateness of lactoferrin as a component of the incubation medium.

The examples are intended to show that lactoferrin can be used in a variety of incubation media, introduced in various amounts.

EXAMPLE 1

1. Isolation of lactoferrin 20 l of cow's milk were centrifuged at $3400 \times g$ for 30 min, and the milk fat was removed in the supernatant. Small amounts of insoluble constituents were removed as sediment and likewise discarded.

The pH of the milk from which the fat had been removed was adjusted to pH 4.0 by addition of hydrochloric acid. The protein precipitate which was produced by this was removed by centrifugation at 3400×g.

The supernatant, which had, after adjustment to pH 5.0 with sodium hydroxide solution, a conductivity of 12 mS/cm at 20° C., was diluted to 7 mS/cm with water and then mixed with 200 ml of the swollen ion exchanger carboxymethylcellulose CM 32 supplied by Whatmann, and the mixture was stirred at room temperature for 4 h. The ion exchanger had previously been equilibrated with 50 mmol/l sodium acetate buffer, pH 5.0. The ion exchanger was then removed by filtration on a suction funnel and suspended in the sodium acetate buffer and transferred into a chromatography column. The column was then washed with 400 ml of the acetate buffer previously described. The proteins bound to the cation exchanger were eluted with a solution of 1 mol/l sodium chloride.

The eluate was adjusted to pH 5.0 with 1-normal sodium hydroxide solution and was converted by dialysis into 50 mmol/l sodium acetate, pH 5.0. The protein mixture was then rechromatographed on 200 ml of carboxymethylcellulose CM 32. The proteins were eluted with a linear gradient from 50 mmol/l sodium acetate, pH 5, to 50 mmol/l sodium acetate, pH 5, and 1 mol/l sodium chloride.

The 4th peak of the elution diagram, whose solution had a conductivity of 18–20 mS/cm, was collected as one fraction, concentrated by ultrafiltration and subjected to gel filtration on ®Sepharose AcA 34 which had been equilibrated with PBS containing 0.5 g/l sodium azide. The main component from the gel filtration, which amounted to 1.2 g of protein, contained the lactoferrin.

2. Comparison of sample dilution buffer containing lactoferrin with sample dilution buffer without addition The Enzygnost® anti HSV ELISA kit of Behringwerke was used for the solid-phase immunometric method. The procedure described in the pack insert was followed for carrying out the assay, and it is described briefly below.

The samples were diluted in the ratio 1:25, instead of 1:44 as recommended, with sample dilution buffer (137 mmol/l NaCl, 7.247 mmol/l $Na_2HPO_4.2H_2O$ and 2.720 mmol/l $KH_2PO_4$ with the addition of 2.7 mmol/l KCl, 0.4 mmol/l $MgCl_2$, 3 mmol/l $NaN_3$, 10 ml/l fetal calf serum and 40 ml/l (®)Tween 20) without or with the addition of 0.2 g/l lactoferrin, and were incubated with the antigens immobilized in the wells of a microassay plate, the unbound antibodies were washed out, an enzyme was bound, using a conjugate solution, to the antibody/antigen complex which had formed, the excess conjugate solution was washed out, a chromogenic substrate solution was used to develop a color via the enzyme, and then the reaction was stopped with a stop solution. The samples which had thus been prepared and had developed a color depending on the content of the virus-specific antibodies were then evaluated by determination of their extinction (E) at 405 nm by photometry.

One portion of each of 9 subjects' sera was heated at 56° C. for 30 min. The other portion remained untreated.

It was found that, in particular, in the case of heated samples in dilution buffer without lactoferrin the extinctions measured in the control wells were very high, but the extinctions in the antigen-coated wells were also raised. This resulted in 5 false-negative results. The control wells are treated ("coated") with the preparation of non-virus-infected cells which are used for obtaining the viruses. When the 9 heated samples were assayed using the dilution buffer containing lactoferrin, no false-negative value was found. The unheated samples were tested using the dilution buffer containing no lactoferrin. The results served to check the results with the heated sera.

EXAMPLE 2

The effect of adding lactoferrin was tested in a single-step sandwich assay. When, in an assay of this type for HBsAg, 7.5 g/l lactoferrin were added, all of 14 unheated critical samples were correctly found to be negative, whereas all had been false-positive determinations without addition of lactoferrin.

EXAMPLE 3

The effect of addition of lactoferrin was tested in a three-step sandwich assay for detecting influenza A antigen. Lactoferrin was used in the second and third steps of this solid-phase immunochemical method.

When, in these two steps, first an antibody/biotin conjugate diluted for use and then a streptavidin/POD conjugate diluted for use and containing lactoferrin (more than 0.05 g/l) were incubated, it was possible to reduce the non-specific reactions, in terms of background and influenza B foreign antigen, by more than 80%. An ELISA result measured at 450 nm is given here as representative:

Non-specific binding without lactoferrin = 2.892 U.
Non-specific binding with lactoferrin = 0.231 U.

In the claims:

1. A method of detecting and determining an antibody or antigen in a biological fluid, comprising the steps of:
    (a) heating said biological fluid;
    (b) diluting said biological fluid with an incubation medium comprising lactoferrin, said lactoferrin being present in said medium substantially isolated from said other milk components and having a concentration in the range of 0.05 to 20 g/l;
    (c) incubating said diluted sample with the conjugate antigen or antibody of said antibody or antigen;
    (d) separating conjugate antibody or antigen bound to antibody or antigen from free conjugate antibody or antigen; and
    (e) determining the amount of the bound conjugate antibody or antigen.

2. The method of claim 1 wherein said incubation medium is an aqueous medium.

3. The method of claim 1 wherein said conjugate antigen or antibody (c) is bound to a solid phase.

4. The method of claim 1 wherein said lactoferrin concentration is in the range of 0.15 to 0.25 g/l.

5. The method of claim 1 wherein said lactoferrin concentration is 0.2 g/l.

6. The method of claim 1 wherein said incubation medium comprises a surfactant.

7. The method of claim 1 wherein said incubation medium has a buffer.

8. The method of claim 1 wherein said incubation medium comprises an additional protein.

9. The method of claim 8 wherein said additional protein is selected from the group consisting of bovine serum albumin, casein, a partially hydrolytically degraded gelatin, a gelatin which has been first hydrolyzed and then chemically crosslinked, and a gelatin which has been first chemically crosslinked and then hydrolyzed.

* * * * *